US009265655B2

(12) United States Patent
Mendius et al.

(10) Patent No.: US 9,265,655 B2
(45) Date of Patent: Feb. 23, 2016

(54) PUNCTUM PLUG INSERTION DEVICE AND DEVICE PACKAGING

(71) Applicant: Enteroptyx, Memphis, TN (US)

(72) Inventors: Richard W. Mendius, Collierville, TN (US); Robert W. Allen, Memphis, TN (US); J. Patrick Ireland, Cordova, TN (US); Connor James Robinson, Memphis, TN (US)

(73) Assignee: Enteroptyx, Memphis, TN (US)

( * ) Notice: Subject to any disclaimer, the term of this patent is extended or adjusted under 35 U.S.C. 154(b) by 177 days.

(21) Appl. No.: 13/910,436

(22) Filed: Jun. 5, 2013

(65) Prior Publication Data

US 2014/0364891 A1    Dec. 11, 2014

(51) Int. Cl.
*A61M 35/00* (2006.01)
*A61F 9/007* (2006.01)

(52) U.S. Cl.
CPC .................................. *A61F 9/00772* (2013.01)

(58) Field of Classification Search
CPC ...................... A61F 9/00772; A61B 17/12022
USPC .................................................. 606/191, 152
See application file for complete search history.

(56) References Cited

U.S. PATENT DOCUMENTS

| 5,282,817 | A  |   | 2/1994  | Hoogeboom et al. |
| 5,741,292 | A  |   | 4/1998  | Mendius |
| 6,234,175 | B1 |   | 5/2001  | Zhou et al. |
| 6,344,047 | B1 |   | 2/2002  | Price et al. |
| 6,527,780 | B1 |   | 3/2003  | Wallace et al. |
| 8,167,939 | B2 |   | 5/2012  | Silvestrini et al. |
| 2003/0093084 | A1 |   | 5/2003  | Nissan et al. |
| 2004/0068286 | A1 | * | 4/2004  | Mendius ........................ 606/191 |
| 2004/0260205 | A1 | * | 12/2004 | Boutillette et al. ............ 600/585 |
| 2011/0196317 | A1 | * | 8/2011  | Lust et al. ....................... 604/290 |
| 2013/0023837 | A1 | * | 1/2013  | Becker ............................ 604/294 |

FOREIGN PATENT DOCUMENTS

| WO | WO2009035567 A2 | 3/2009 |
| WO | WO2012144980 A1 | 10/2012 |

OTHER PUBLICATIONS

2010 FCI Ophthalmics Product Catalog, www.fci-ophthalmics.com.

\* cited by examiner

*Primary Examiner* — Richard Louis
(74) *Attorney, Agent, or Firm* — Gordon & Jacobson, P.C.

(57) ABSTRACT

A punctum dilating and plug inserting system includes an inserter and a protective cover defining a dilator. The inserter includes a longitudinal body, and a handle. The handle has a rounded stationary member and a trigger rotatably connected to the handle by a living hinge. A mounting wire extends through the body and is connected to the trigger. When the trigger is activated, the wire is retracted and a plug mounted on a distal end of the wire is released. A packaging is provided for receiving, protecting, and handling at least a portion of the entire inserter until ready for use. An end of the packaging includes a dilator dip for dilating the punctum in advance of receiving the punctum plug.

20 Claims, 2 Drawing Sheets

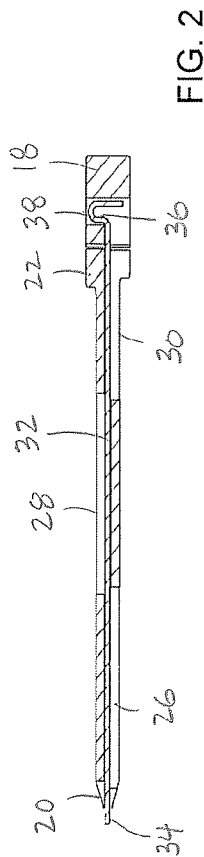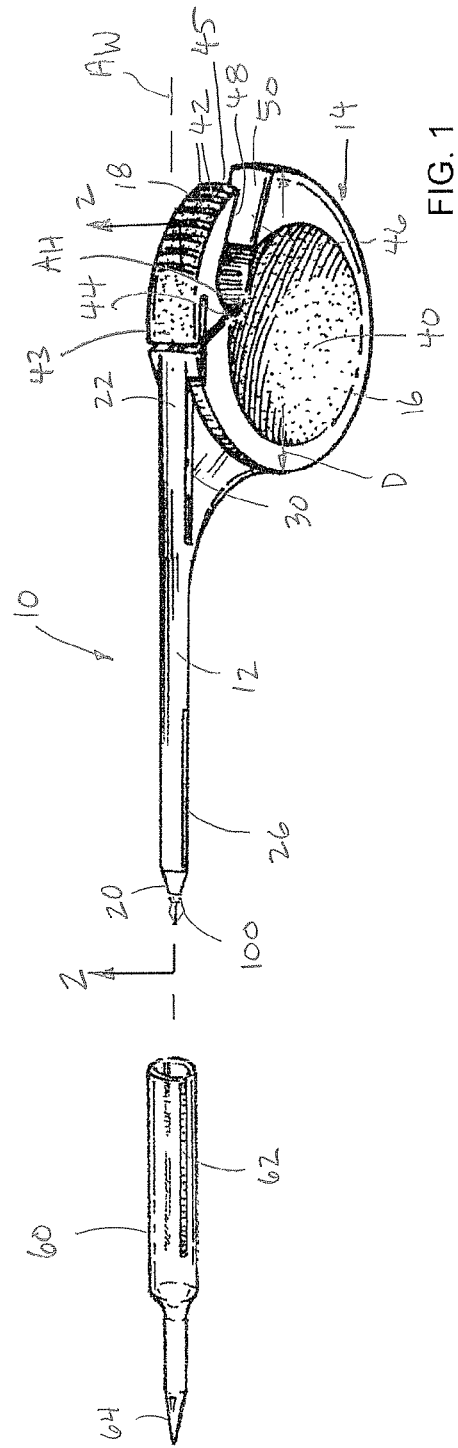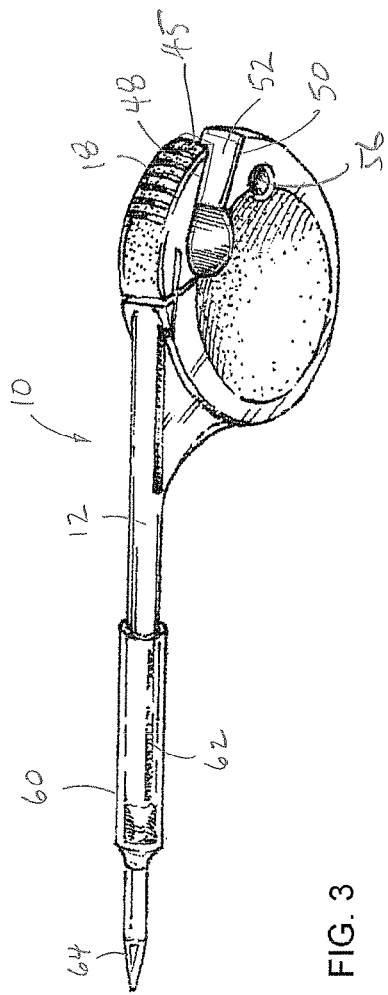
FIG. 1
FIG. 2
FIG. 3

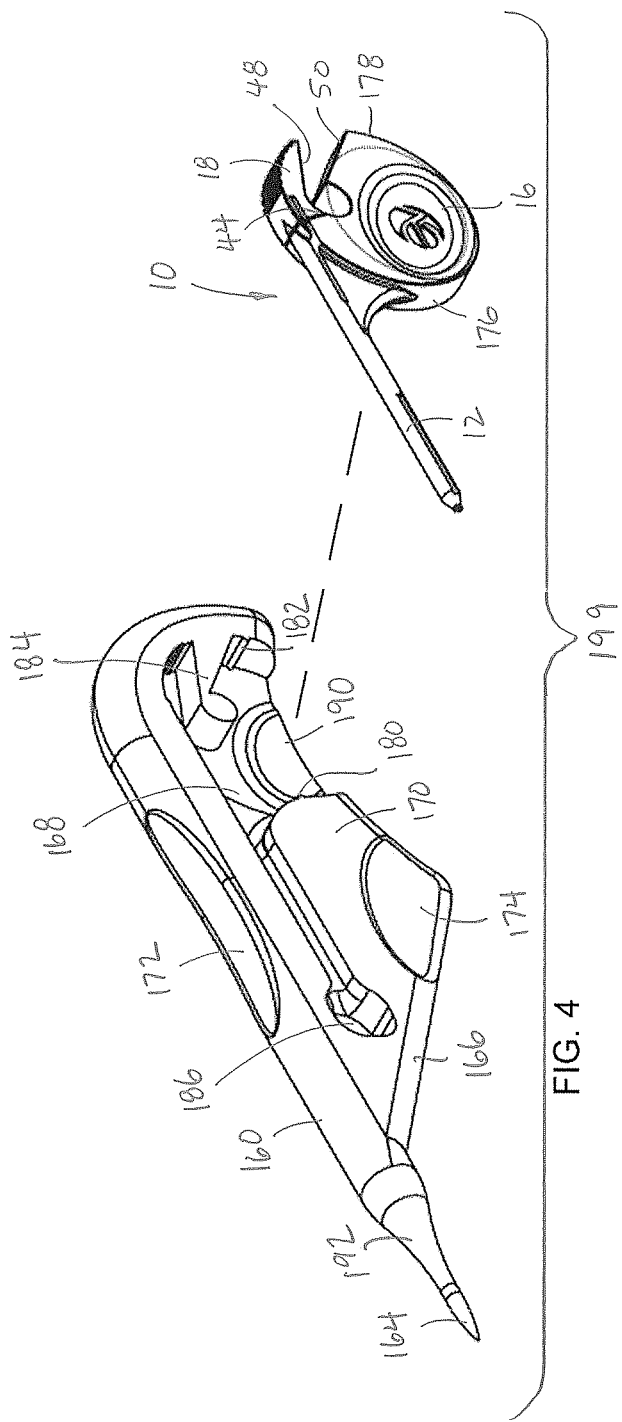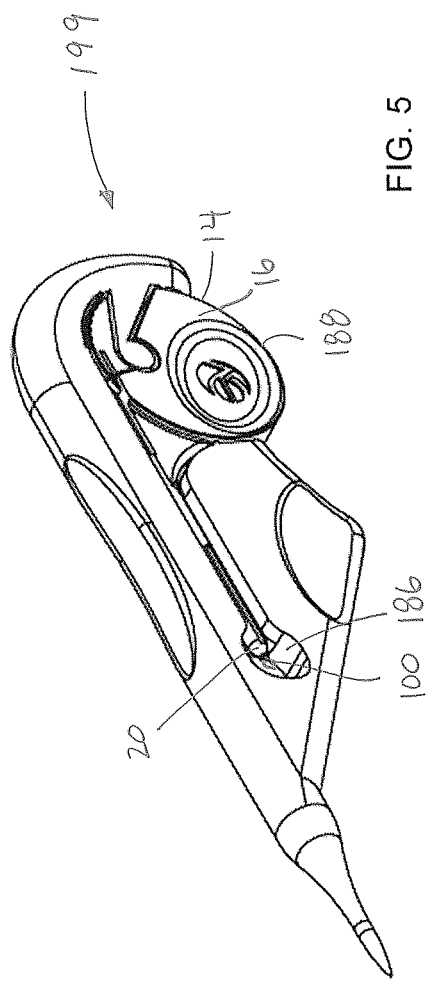
FIG. 4
FIG. 5

PUNCTUM PLUG INSERTION DEVICE AND DEVICE PACKAGING

BACKGROUND OF THE INVENTION

1. Field of the Invention

The present invention relates broadly to medical instruments. More specifically, this invention relates to instruments for inserting a punctum plug and a packaging for such instruments.

2. State of the Art

The surface of the eye and the inner surface of the eyelid are moisturized by tears constantly produced by glands around the eye. A tiny hole, known as the lacrimal punctum, at the inner corner of each upper and lower lid margin drains the tears away through ducts for proper circulation.

Patients, including contact lens wearers, who suffer from dry eye, or insufficient tear production, experience a great deal of discomfort because of insufficient lubrication between the lens and the surface of the eye. One solution is to occlude or block the lacrimal duct to prevent tear drainage. Permanent lacrimal occlusion can be performed surgically, typically by closing the punctal opening, whereas reversible occlusion can be performed by inserting a tiny plug into a portion of the lacrimal duct, such as the punctum. A typical punctum plug includes a cylindrical or frustoconical body, a larger head portion to retain the plug at the punctal opening, and a coaxial bore through the head portion and partially through the body at which the plug is coupled to the tip of an instrument during insertion.

A variety of instruments are available for inserting lacrimal occluders such as punctum plugs and canalicular implants. For example, Lacrimedics, Inc. of Rialto, Calif., has sold a canalicular implant preloaded on the tip of a wire stuck into a piece of foam. The wire is used to push the implant into the canaliculus. After the implant is deeply seated, the wire is withdrawn.

EagleVision, Inc. of Memphis, Tenn. sells the EP2 punctum plug inserter and dilator which is described in U.S. Pat. No. 5,741,292 to Mendius. This more complex device for punctal dilation and insertion includes a cylindrical body having a plug inserting tip at one end and an opposite punctum dilating end. An elongated button is arranged longitudinally along the body, and includes a slidable end and a fixed end positioned between the slidable end and the plug inserting tip. The button has an outwardly bowing inner surface spaced from the body such that when the button is pressed toward the body, the slidable end slides away from the plug inserting tip. A plug mounting wire is fixedly attached to the slidable end of the button, and slidably extends within the body and protrudes out of the plug inserting tip. A conventional punctum plug is attached to the protruding end of the wire. The mounting wire can be retracted by pressing on a button at a location between the proximal and distal ends of the mounting wire and thereby effect release of the plug.

In operation, one hand of the physician is placed against the face of a plug recipient, and the lid of the eye receiving the plug is pulled down to expose the punctal opening. The instrument is held in the other hand and the dilating tip is used to dilate the punctum. The instrument must then be turned around so that the plug inserting tip is now facing the eye, and the plug can then be inserted into the dilated punctum. It is noted that the device must be turned around carefully to prevent inadvertently dropping the instrument and to prevent unwanted contact with the plug (which may contaminate or dislodge the plug). Moreover, it must be turned around quickly, as the punctal opening begins to constrict within approximately five seconds after dilation. Once the plug is positioned in the punctum, the plug is released from the instrument by depressing the buttons, which retracts the wire and frees the plug.

FCI Ophthalmics of Marshfield Hills, Mass. sells a Ready-Set™ punctum plug system which also includes a plug inserter and punctal dilator instrument. The instrument is generally similar to the Mendius device, but includes a two-sided trigger with handles located on diametrically opposite sides of the body. When the handles are pressed toward a plug mounting pin and one another, the pin is retracted into the body, thereby dislodging the plug from the pin.

US Pub. No. 2004/0068286, also to Mendius, teaches a plug insertion instrument having a protective dilating cap covering the plug. The punctal opening can be dilated with the cap, and then the cap is removed to expose the plug at the same end as the dilator so that the plug can then be conveniently inserted into the punctum. The plug is deployed by pressing on a button attached to a proximal end of a plug mounting wire, with the plug mounted at the distal end of the wire. The button is pressed at a location between the proximal and distal ends of the wire to retract the wire and effect release of the plug.

SUMMARY OF THE INVENTION

In accord with the invention, a punctum dilating and plug inserting system includes an inserter and a protective cover defining a dilator. The inserter includes a longitudinal body defining a stable pathway therethrough and having a tapered tip, and a handle coupled to the body. The handle has a stationary member fixed relative to the body, and at most one trigger. The trigger is coupled to the body by a living hinge. A mounting wire extends through the body and has a distal end that extends beyond the tapered tip and a proximal end that is coupled to the trigger. The distal end of the mounting wire is adapted to receive a punctum plug. Movement of a free end of the trigger relative to the stationary member about the living hinge causes retraction of the wire relative to the longitudinal body to result in sufficient withdrawal of the wire into the body to result in release of the plug from the inserter.

In one aspect of a preferred embodiment, the stationary member of the handle is rounded with a diameter extending parallel to the axis of the mounting wire. In another aspect of a preferred embodiment, the longitudinal body extends substantially along a tangent to a circumference to the stationary member of the handle. In another aspect of the invention, the stationary member of the handle has concave sides to facilitate gripping by a user. The trigger preferably also includes a textured surface to facilitate manipulation.

In another preferred aspect of the invention, the living hinge is located spaced apart from the axis of the wire, and is fixed in location as the trigger is rotated. The stationary member defines a stop for the trigger. In accord with a preferred aspect of the invention, a leaf spring may be provided to return the trigger to a starting position for re-use of the inserter, should such be desired.

The cover is removably coupled over a portion of the instrument including the plug. In one embodiment, the cover is a cap friction fit over an end of the longitudinal body to enclose the punctum plug on the wire. The cap tapers to form a dilator sized to be inserted into the punctum to dilate the punctum. After the cap is used to perform dilation, the cap can be readily removed from the end of the body to expose the plug for insertion. In another embodiment, the cover is a packaging for receiving, protecting, and handling substantially the entire inserter until ready for use. The packaging is formed from a relatively rigid plastic and defines a body having that receives the inserter, and a distal end that tapers to the dilator. The cavity includes a dedicated portions that closely receive the longitudinal body of the inserter, the stationary member of the handle, and the trigger in a manner that prevents relative movement of such portions to each other while the inserter is retained within the packaging. The cavity also includes an enlarged area spaced about the distal end of the longitudinal body and the plug to prevent any contact therewith that could result in damage to or dislodgement of the plug from the inserter. In each embodiment, the cover structure defining the dilator provides a protective enclosure for a plug loaded on the mounting wire until the cover and inserter are decoupled.

The inserter of the invention may be operated by a physician as follows. In the embodiment in which the dilator is formed by a cap fit over the distal end of the longitudinal body, the physician holds the inserter in a first hand, and places a second hand on a cheek of the plug recipient and retracts the eyelid to expose the punctal opening. With the punctal opening exposed, the physician moves the dilator tip of the cap into the punctal opening, dilates the opening, and then withdraws the tip. Then, the cap is removed from the inserter, and the inserter is then again maneuvered to the punctal opening and the plug is inserted therein. In the embodiment in which the cover is in the form of a packaging in which the inserter is retained, the physician holds the packaging in a first hand, and places a second hand on a cheek of the plug recipient and retracts the eyelid to expose the punctal opening. With the punctal opening exposed, the physician moves the dilator tip of the packaging into the punctal opening, dilates the opening, and then withdraws the dilator tip. Then, the inserter is removed from the packaging and the inserter is advanced toward the punctal opening and the plug is inserted therein.

Once the plug has been inserted into the dilated punctal opening, the trigger is pressed so that it is rotated about the hinge, with the free end of the trigger rotated away from the axis of the mounting wire, to thereby withdraw the wire from the plug and release the plug into the punctum. After the plug has been released, the inserter and/or cover can be re-used. Where the inserter is provided with the leaf spring between the trigger and the stationary member of the handle, the inserter is particularly well adapted for a defined return of the trigger for re-use.

Additional objects and advantages of the invention will become apparent to those skilled in the art upon reference to the detailed description taken in conjunction with the provided figures.

BRIEF DESCRIPTION OF THE DRAWINGS

FIG. 1 is a perspective assembly view of a punctum plug inserter and protective cap according to a first embodiment of the invention.

FIG. 2 is a longitudinal section view across line 2-2 in FIG. 1, shown without the punctum plug.

FIG. 3 is a perspective assembled view of the punctum plug inserter with protective cap according to the first embodiment of the invention.

FIG. 4 is a perspective assembly view of a punctum plug inserter and protective packaging according to a second embodiment of the invention.

FIG. 5 is a perspective assembled view of the punctum plug inserter with protective packaging according to the second embodiment of the invention.

DETAILED DESCRIPTION OF THE PREFERRED EMBODIMENTS

Referring to FIGS. 1 and 2, a punctum plug inserting instrument 10 includes a longitudinally extending body 12, and a handle 14 defining a stationary member 16 and a single rotatable trigger 18 integrally molded with the body 12 such that the body, the stationary member, and trigger are a unitarily construct. Such construct is preferably made of a polymeric material.

The longitudinal body 12 is preferably cylindrical, and has a preferably frustoconically tapered distal end 20 and a proximal end 22. While the body is most preferably straight, it can alternatively include a curved distal portion to facilitate access to the punctum. A stable pathway is defined between its proximal and distal ends. The pathway can be defined by a bore, optionally with an inserted cannula. More preferably, the pathway (as shown) is defined by a series of alternating lateral slots 26, 28, 30 that extend along the length of the body to result in a pathway defined in size for stable retention and controlled longitudinal displacement of a mounting wire 32 positioned within the pathway. The mounting wire 32 has a distal end that extends sufficiently beyond the tapered tip 20 (at 34) to have a punctum plug 100 mounted thereon, and a bent proximal end portion 36 is coupled to the trigger 18, preferably captured within a defined recess 38 in the trigger. Movement of the trigger 18 relative to the stationary member 16 causes retraction of the wire 32 relative to the longitudinal body 12 to result in sufficient withdrawal of the wire into the body to result in release of a plug 100 mounted on the inserter 10. The trigger 18 is pressed at a location proximal of the proximal end portion 36 of the mounting wire to effect movement of the mounting wire 32 relative to the distal end of the body 12. The trigger 18 preferably includes a textured surface, e.g., includes ribs 42, at this location to facilitate stable manipulation thereof.

The stationary member 16 is stiff and substantially thicker than the longitudinal body 12 and includes concave sides 40, both features to facilitate stable handling by a user. The stationary member 16 is preferably rounded, and more preferably defines a diameter D that extends parallel to the wire axis AW of the mounting wire 32. The stationary member 16 is preferably laterally offset to one side of the longitudinal body 12. In a preferred embodiment, the longitudinal body 12 extends substantially along a tangent to an outer circumference to the rounded stationary member 16 of the handle. The trigger 18 is preferably the same thickness as the stationary member and preferably extends as a continuation of the outer circumference. As such, the stationary member and the trigger together assume a substantial area of a closed rounded shape, such as a circle or oval. The trigger is substantially stiff and preferably not subject to deformation as it is rotated about the hinge axis. The trigger 18 includes a first end 43 and a free second end 45.

The first end 43 of the trigger 18 is connected to the stationary member 16 by a living hinge 44 and is located adjacent the proximal end 22 of the longitudinal body 12. The living hinge 44 is located spaced apart from the wire axis A of the wire 32, and is fixed in location as the trigger 18 is rotated on its hinge axis AH relative to the stationary member 16. The hinge axis AH is oriented orthogonal to the wire axis AW and is located at one side of said wire axis, whereas the trigger 18 can be pressed at a location situated along an opposite side of the wire axis AW to initiate rotation of the trigger about the hinge axis AH to move the second end 45 of the trigger 18 toward the stationary member 16.

The stationary member 16 defines a stop 46 for the trigger 18. More particularly, the lower surface 48 of the trigger and the upper face 50 of the stop 46 are angled relative to each other in the pre-actuated configuration (seen best in FIG. 4 discussed below). As the trigger 18 is pressed, the lower surface 48 of the trigger is rotated into substantially planar contact against the upper stop face 50 to provide a positive indication that the mounting wire has been fully retracted. In accord with another aspect of the invention, turning to FIG. 3, a metal leaf spring 52 optionally may be provided between the trigger 18 and the stationary member 16, preferably retained along the lower surface 48 and upper stop face 50, to cause automatic to return of the trigger 18 to a starting position in which the distal end of the mounting wire 32 extends from the distal end of the body 12. The leaf spring 52 particularly adapts the inserter 10 for re-use, should such be desired, as it provides consistency and repeatability to the hinge and trigger action for multiple uses.

Referring to FIG. 3, the stationary member 16 optionally may be formed with mating structure for detachably coupling a plurality of inserters 10 in a side-by-side arrangement. Female mating structure 56 is provided at one side of the stationary member 16, whereas male mating structure (not shown) is provided at the opposite side. The mating structure may include an interference fit or snap fit that permits ready release of coupled inserters, but provides a sufficient number of inserters together as needed for an individual patient procedure.

In accord with a preferred aspect of the invention, a distinct cover structure incorporating a dilator is removably coupled to a portion of the inserter 10, and covers the plug 100 mounted on the mounting wire 34. Referring now to FIGS. 2 and 3, in one embodiment, the cover structure is a cap 60 that can be friction fit over a distal portion of the body 12. Other means of coupling the cap to the inserter may be used, including threads and a releasable interlock. The cap 60 may include longitudinal slits 62 about which the cap resiliently expands to receive and capture and the body for retention thereon. The cap 60 tapers to form a dilator 64 preferably in the form of a substantially conical tip that is sized to be inserted into the punctum to dilate the punctum. The cap can be readily removed from the distal portion of the body to expose the plug for insertion.

The system of the invention may be operated by a physician as follows. The physician holds the inserter 10 in a first hand, and places a second hand on a cheek of the plug recipient and retracts the eyelid to expose the punctal opening. With the punctal opening exposed, the physician moves the dilator 64 of the cap 60 into the punctal opening, dilates the opening, and then withdraws the dilator from the opening. The cap 60 is then removed from over the distal end of the inserter 10, and the inserter is then again maneuvered to the dilated punctal opening and the plug is inserted therein. The trigger 18 is then pressed so that it is rotated about the living hinge 44, with the free end 45 of the trigger 18 rotated away from the axis A of the mounting wire 32, to thereby withdraw the wire from the plug 100 and release the plug into the punctum. After the plug 100 has been released, the inserter 10 and/or cap 60 can be re-used. Where the inserter 10 is provided with the leaf spring 52 between the trigger 18 and the stationary member 16 of the handle, the inserter is particularly well adapted for a defined return of the trigger for re-use.

The procedure is repeated for the insertion of each punctum plug 100, optionally with a different inserter 10 and cap 60 for each punctum. However, it is within the scope of the invention that the inserter 10 be reloaded by a user with plugs from a store of plugs so that the inserter can be used on more than one punctum of a patient and that the cap be repositioned over the distal portion of the inserter in preparation for subsequent use, even on the same patient. Before use on a different patient it is necessary to re-sterilize the inserter and cap.

Turning now to FIGS. 4 and 5, an alternative cover structure 160 incorporating a dilator 164 can be coupled to a portion of the inserter 10 to define a packaged inserter system 199. The cover structure 160 is a rigid packaging in which the instrument 10 is protectively received and retained until ready for use. The packaging is formed from a relatively rigid polymer and defines a body portion 166 having a single open cavity 168 in the side 170 thereof shaped and otherwise adapted to receive the inserter 10, an upper external finger grip 172, and a lower finger grip 174 on the side 170 of the body portion 166 defining the cavity 168. More particularly, the cavity 168 has a portions that closely receive the longitudinal body 12 of the inserter, and the distal and proximal sides 176, 178 of the stationary member 16 of the handle. Specifically, the distal and proximal sides 176, 178 of the stationary member 16 of the handle may be engaged by ribs 180, 182 defined within the cavity that facilitate an interference with the inserter. The cavity 168 is further shaped to retain the trigger 18 in a pre-actuation configuration, with the positive space 184 between the trigger 18 and stationary member 16 having sufficiently close tolerance to prevents movement of such portions relative to each other while the inserter 10 is retained within the cover structure 160. The cavity 168 also includes an enlarged area 186 spaced about the distal end 20 of the longitudinal body 12 and the plug 100. The enlargement minimizes the opportunity for any contact between the plug and the cover structure 160 during insertion and removal of the inserter 10 relative to the cover structure 160 that could otherwise result in damage to or dislodgement of the plug 100 from the inserter 10. A lower portion 188 of the stationary member 16 extends out of the bottom of the cavity 190 to facilitate removal of the inserter from the cover structure 160; i.e., so that the stationary member 16 can be gripped to pull the inserter up and out of the cover structure. The cover structure 160, at a distal end 192 (distal of the cavity 168) defines the dilator 164 in the form of a tapered nose portion sized to be inserted into and dilate the punctal opening.

The inserter 10 of the invention may be operated by a physician as follows. The physician holds the inserter 10 in a first hand, and places a second hand on a cheek of the plug recipient and retracts the eyelid to expose the punctal opening. With the punctal opening exposed, the physician moves the dilator 164 of the packaging 160 into the punctal opening, dilates the opening, and then withdraws the dilator from the opening. The inserter 10 is then removed from within the packaging 160 by lifting the lower portion 188 of the stationary member 16 of the handle 14 relative to the body 166 of the packaging. The inserter 10 is then used as described above, with each of the inserter and packaging 160 being capable of re-sterilization and re-usable.

In either embodiment, the distinct cover defining the dilator provides a protective enclosure for a plug loaded on the mounting wire until the protective structure and the inserter are decoupled, with the cover of the second embodiment further preventing actuation of the inserter until the cover is removed and further providing a body for manipulation of the dilator.

There have been described and illustrated herein embodiments of a punctum plug inserter and protecting cover therefor, as well as method of using the same. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A punctum plug insertion system for inserting and releasing a punctum plug into a punctal opening of an eye, comprising:
   a) a longitudinally extending body having a proximal end and a distal end and defining a pathway between said proximal and distal ends;
   b) a handle having a stationary member fixed to said proximal end of said body, and a trigger, said stationary member disc-like in shape, having a circumference, and defining a diameter across said disc-like stationary member, and said trigger having a first end and a free second end, said handle further having a living hinge rotatably connecting said first end of said trigger to said stationary member; and
   c) a plug mounting wire extending from beyond said distal end of said body, through said pathway, and to said trigger, said wire having a distal end onto which the punctum plug can be mounted, and a proximal end retained relative to said trigger, said wire defining a wire axis, said wire axis and said diameter of said stationary member extending in a common plane and parallel to each other,
   said body, handle and wire together defining an inserter for the plug,
   wherein when a user holds said stationary member and rotates said free second end of said trigger away from said wire axis, said wire is displaced relative to said stationary member such that said distal end of said mounting wire is retracted relative to said distal end of said body to release the plug.

2. The punctum plug insertion system according to claim 1, wherein:
   said body joins said stationary member at a tangent of said circumference.

3. The punctum plug insertion system according to claim 1, wherein:
   said stationary member and said trigger have a common thickness.

4. The punctum plug insertion system according to claim 1, wherein:
   said trigger is substantially stiff and not subject to deformation as said trigger is rotated about said hinge axis.

5. The punctum plug insertion system according to claim 1, wherein:
   at least one of said trigger and said stationary member include a stop for limiting motion of said trigger relative to said stationary member.

6. The punctum plug insertion system according to claim 5, wherein:
   said stop comprises a lower surface of said trigger and an upper face of said stationary member which are moved into contact when said distal end of said mounting wire is moved a sufficient distance relative to said distal end of said body to release the punctum plug mounted thereon.

7. The punctum plug insertion system according to claim 6, wherein:
   when said mounting wire is moved said sufficient distance, said lower surface and said upper face are in substantially planar contact.

8. The punctum plug insertion system according to claim 1, further comprising:
   a leaf spring operably coupled between said trigger and said stationary member to provide a return force to said trigger.

9. The punctum plug insertion system according to claim 1, further comprising:
   a removable cover coupled to a portion of said inserter, said cover defining a punctal dilator, and said cover at least partially surrounding said distal end of said longitudinal body and the plug when coupled to said inserter.

10. The punctum plug insertion system according to claim 9, wherein:
    said cover is a rigid packaging defining a body portion having a side and an open cavity in said side into which said inserter is received.

11. A punctum plug insertion system for inserting and releasing a punctum plug into a punctal opening of an eye, comprising:
    a) a longitudinally extending body having a proximal end and a distal end and defining a pathway between said proximal and distal ends;
    b) a handle having a stationary member coupled to said proximal end of said body, and a trigger, said stationary member rounded in shape, having a circumference, and defining a diameter, and said trigger having a first end and a free second end, said handle further having a living hinge rotatably connecting said first end of said trigger to said stationary member;
    c) a plug mounting wire extending from beyond said distal end of said body, through said pathway, and to said trigger, said wire having a distal end onto which the punctum plug can be mounted, and a proximal end retained relative to said trigger, said wire defining a wire axis, said wire axis and said diameter of said stationary member extending in a common plane,
    said body, handle and wire together defining an inserter for the plug,
    wherein when a user holds said stationary member and rotates said free second end of said trigger away from said wire axis, said distal end of said mounting wire is retracted relative to said distal end of said body to release the plug; and
    d) a removable cover coupled to a portion of said inserter, said cover including a rigid packaging defining a body portion having a side and an open cavity in said side into which said inserter is received, and structure extending between said trigger and stationary member that retains said trigger against movement relative to said stationary member.

12. A punctum plug insertion system for inserting and releasing a punctum plug into a punctal opening of an eye, comprising:
    a) a longitudinally extending body having a proximal end and a distal end and defining a pathway between said proximal and distal ends;
    b) a handle having a stationary member coupled to said proximal end of said body, and a trigger, said stationary member rounded in shape, having a circumference, and defining a diameter, and said trigger having a first end and a free second end, said handle further having a living hinge rotatably connecting said first end of said trigger to said stationary member;
    c) a plug mounting wire extending from beyond said distal end of said body, through said pathway, and to said trigger, said wire having a distal end onto which the punctum plug can be mounted, and a proximal end retained relative to said trigger, said wire defining a wire axis, said wire axis and said diameter of said stationary member extending in a common plane, said body, handle and wire together defining an inserter for the plug, wherein when a user holds said stationary member and rotates said free second end of said trigger away from said wire axis, said distal end of said mounting wire is retracted relative to said distal end of said body to release the plug; and d) a removable cover coupled to a portion of said inserter, said cover including a rigid packaging defining a body portion having a side and an open cavity in said side into which said inserter is received, said cavity is a well in said cover, said well shaped to receive said inserter in an interference fit.

13. The punctum plug insertion system according to claim 12, wherein:

said cavity defines an enlarged space about said distal end of said longitudinal body and the plug.

14. The punctum plug insertion system according to claim 12, wherein:

said cavity defines a lower opening through which a lower portion of said stationary member extends, thereby facilitating removal of said inserter from said packaging.

15. The punctum plug insertion system according to claim 10, wherein:

said dilator is in the form a tapered nose distal of said cavity.

16. A punctum plug insertion system for inserting and releasing a punctum plug into a punctal opening of an eye, consisting of:

a) a longitudinally extending body having a proximal end and a distal end and defining a pathway between said proximal and distal ends;

b) a handle having a disc-like stationary member fixed to said proximal end of said body, and a trigger, said trigger having a first end and a free second end, and a living hinge rotatably connecting said first end of said trigger to said stationary member, said stationary member and said trigger together defining a shape with a rounded periphery, and wherein said periphery has an opening through which said trigger can be displaced; and c) a plug mounting wire extending from beyond said distal end of said body, through said pathway, and to said trigger, said wire having a distal end onto which the punctum plug can be mounted, and a proximal end retained relative to said trigger, said body, handle and wire together defining an inserter for the plug, wherein when a user holds said stationary member and presses said trigger at a location proximal of said stationary member and proximal of said proximal end of said mounting wire such that said free second end of said trigger is moved toward said stationary member, said distal end of said mounting wire is retracted relative to said distal end of said body to release the plug.

17. A punctum plug insertion system for inserting and releasing a punctum plug into a punctal opening of an eye, consisting of:

a) a longitudinally extending body having a proximal end and a distal end and defining a pathway between said proximal and distal ends;

b) a handle consisting of,
(i) a stationary member fixed to said proximal end of said body so as to be longitudinally offset from said body, and
(ii) a trigger having a first end and a free second end, said first end located adjacent said proximal end of said body,
said stationary member and said trigger together defining a disc-like shape with a periphery, and wherein said periphery has an opening through which said trigger can be displaced,
(iii) a living hinge rotatably connecting said first end of said trigger to said stationary member, and
(iv) a spring located between said trigger and said stationary member; and c) a plug mounting wire extending from beyond said distal end of said body, through said pathway, and to said trigger, said wire having a distal end onto which the punctum plug can be mounted, and a proximal end retained relative to said trigger, said wire defining a wire axis, said body, handle and wire together defining an inserter for the plug, wherein when a user holds said stationary member and rotates said free second end of said trigger away from said wire axis, said distal end of said mounting wire is retracted relative to said distal end of said body to release the plug.

18. A punctum plug insertion system according to claim 17, wherein:

said stationary member and said trigger have a common thickness.

19. The punctum plug insertion system according to claim 1, wherein:

said trigger forms a portion of said circumference of said disc-like shape of said stationary member.

20. The punctum plug insertion system according to claim 8, wherein:

said disc-like shape of said stationary member extends within a plane, and said spring extends within said plane.

* * * * *